United States Patent [19]
Johnson

[11] 4,058,112
[45] Nov. 15, 1977

[54] HEAD POSITIONER AND ARM REST FOR EYE SURGERY

[76] Inventor: Robert M. Johnson, P.O. Box 525, Kirkland, Wash. 98033

[21] Appl. No.: 715,651

[22] Filed: Aug. 19, 1976

[51] Int. Cl.² .............................................. A61B 19/00
[52] U.S. Cl. ...................................... 128/1 R; 5/338; 269/328; 128/133
[58] Field of Search .................. 128/1 R, 132 R, 133, 128/134; 269/322, 328; 5/337, 338

[56] References Cited

U.S. PATENT DOCUMENTS

| | | | |
|---|---|---|---|
| 1,967,067 | 7/1934 | Rightmire | 5/337 X |
| 3,347,544 | 10/1967 | Uffenorde | 269/328 |
| 3,897,777 | 8/1975 | Morrison | 128/133 |

FOREIGN PATENT DOCUMENTS

| | | | |
|---|---|---|---|
| 2,430,213 | 1/1976 | Germany | 5/338 |
| 178,046 | 2/1966 | U.S.S.R. | 269/328 |

Primary Examiner—Dalton L. Truluck

[57] ABSTRACT

A right rectangular block of resilient material is provided with a recess or cavity, open top to bottom, shaped to embrace and position an eye patient's head on an operating table. Laterally disposed horizontal surfaces contiguous with the upper end of the cavity or recess serve as arm and hand and instrument supports coplanar with a surgical situs of the eye, established during preparation for surgery.

1 Claim, 4 Drawing Figures

HEAD POSITIONER AND ARM REST FOR EYE SURGERY

SUMMARY OF THE INVENTION

Eye surgery is among the most, if not the most, meticulous, delicate and difficult of operations practiced by surgeons. It is common practice for the surgeon and his assistant scrub nurse to continuously employ dual miscroscopes and to conduct the operation without removing their eyes from the ocular eye pieces. It is required that the surgical instruments be arrayed and in the immediate proximity of the surgical situs so that almost totally by feel they may be located and passed from hand to hand and from person to person. It is imperative further that the surface supporting the instruments be sterile and one that minimizes if not fully eliminates infection caused by strike-through which is a condition that develops in or on a surgical drape over a non-sterile surface that has been wetted by saline solution or blood. The wetted drape will transmit infection residing beneath the drape as, for example, on the patient himself.

Such surgery is also time-consuming and very tiring to the surgeon. When no wrist or arm support is used, the surgeon must tense his muscles and lock his wrists in his efforts to restrict motion to his fingers as he manipulates his instruments. In some instances rigid rests have been provided to support the surgeon's forearms and wrists in the vicinity of the surgical situs. These, however, do not operate to provide support contiguous with the patient's eye as is desirable. In addition, it has been found that rigid rests subject the surgeon to discomfort due to his continuously bearing down on the non-yielding rests for long periods of time. The pressure is applied at a restricted or localized area of his forearm and he soon senses pain but seldom can he relieve it by moving his arm to another locality.

In the past it has been recognized that the eye patient's head must be immobilized during surgery and some attempts have been aimed at accomplishing this objective. One such is described in the Uffenorde U.S. Pat. No. 3,347,544 wherein a resilient block of resilient material is provided with a shallow, resilient bottom recess to receive the patient's head and upper neck to just below the ears. It is unknown to confine the sides of the patient's head to a point substantially coplanar with the surgical situs which, naturally, is the plane that includes the patient's eye. Unless the patient's head is restrained against side-to-side movement, involuntary reflexive reactions, especially when surgery is conducted under local anesthesia, can occur to the detriment of the operation and the patient's well-being.

It is therefore been among the primary objects of this invention to provide: means to embrace and immobilize an eye patient's head during delicate and protracted surgery; means serving as a comfortable arm and hand rest for the surgeon operable at very close proximity to the surgical situs; means functioning as a superior support platform for the surgeon's ocular instruments and for intraocular lens and corneal buttons closely available to the operative field; and a support platform means that isolates the surgical area from possible contamination and minimizes if not eliminates possible infection of the surgeon's instruments and gloved hands due to strike-through.

These and other objects and advantages of this invention will become apparent during the course of the following detailed description in which is disclosed a preferred embodiment of the invention.

DETAILED DESCRIPTION

Figure 1:
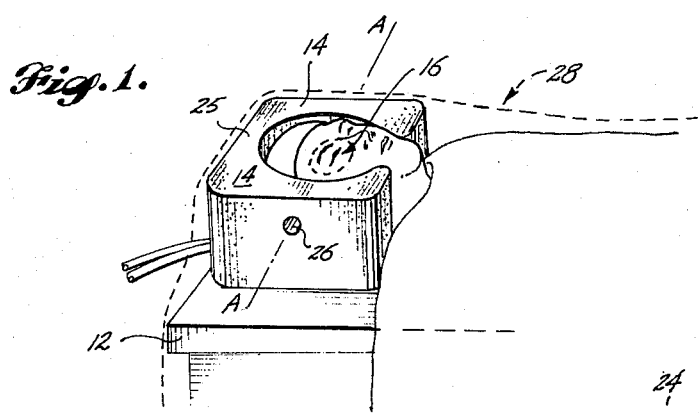
FIG. 1 is a perspective view showing the head positioner for eye surgery in use.
Figure 2:
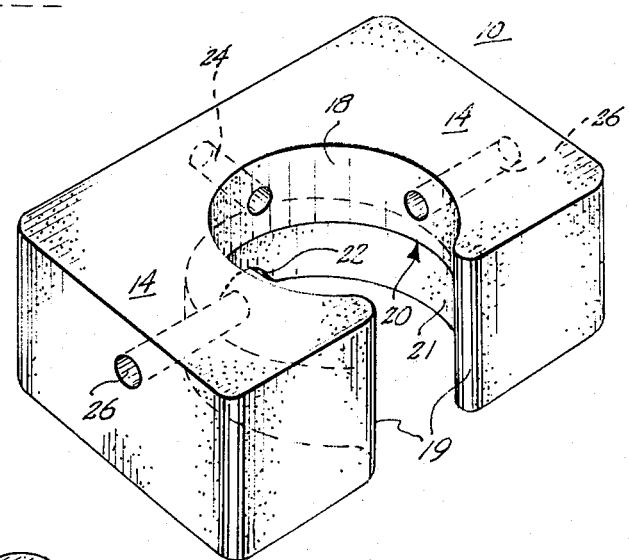
FIG. 2 is an enlarged perspective view of the upper side of the head positioner.

In FIG. 1 the head positioner and arm rest 10 of this invention is shown supported on the head-end of a surgical table 12 upon which the patient lies. The positioner 10 has a top-to-bottom recess that permits it to surround the top and sides of the patient's head and upper neck. Laterally extending support surfaces 14, 14 lie in or very close to the plane A—A in which the patient's eye 16 is disposed.

Figure 3:
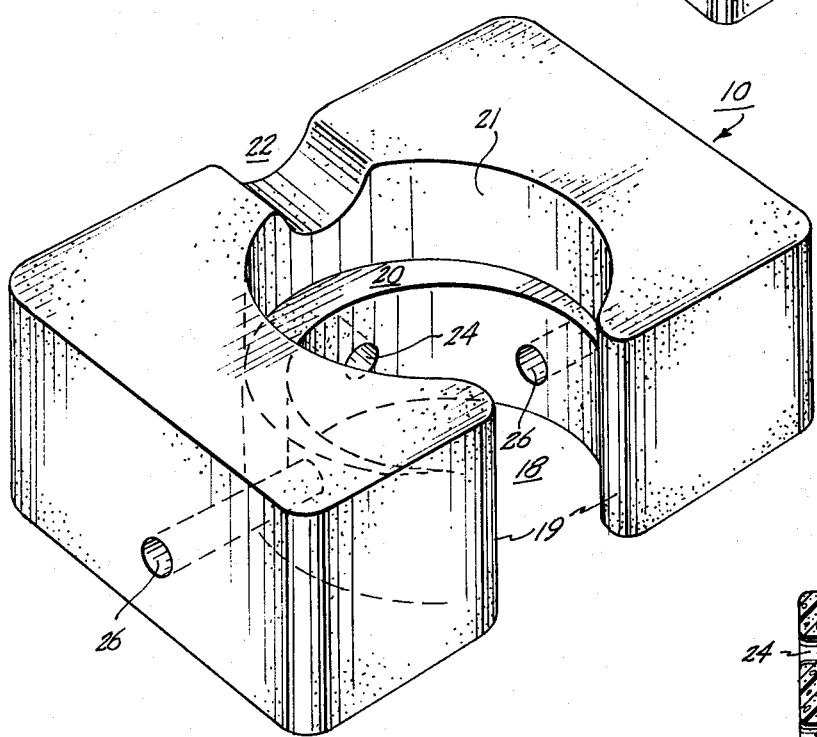
FIG. 3 is an enlarged perspective view of the underside of the head positioner.
Figure 4:
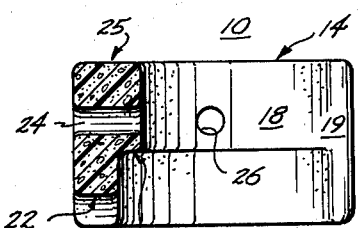
FIG. 4 is a cross-sectional view taken in the vertical plane bisecting the head positioner between its ends.

Referring to FIG. 3, the positioner/rest 10 will be seen to comprise a substantially right-rectangular block of urethane foam or other resilient material. Block 10 has formed therein the open-sided, head-receiving recess or cavity 18 which embraces and comfortably secures the patient's head and portions of the neck. Recess/cavity 18 is open top and bottom. The patient's head is otherwise supported. At its lower rear, cavity 18 is thinned or cut away at 21 to form overhanging ledge 20 and insure low in block 10 air space for ventilation purposes and space to accommodate head-supporting cushions and the like. Passage 24 extends through the closed end 25 of cavity 18. Side passages 26, 26 communicate laterally outward from cavity 18.

Passages 24 and 26, 26 facilitate ventilation between cavity 18 and the surrounding atmosphere, permitting the withdrawal of irritating or combustive gases that may be employed by the anesthetist. Notch 22 accommodates cords and tubes installed between the patient and anesthetic- and monitoring apparatus usually employed by an attending anesthetist.

The block 10 is preferably about seven inches thick, twelve inches wide and about twenty inches long. The recess or cavity 18 is shaped and sized to receive the patient's head and neck. The size of cavity will vary in accordance with the dimensions of various patients. The preferred seven inches of thickness of block 10 is at least, but usually greater than, the distance between the plane of a patient's eye and the back of the head. Thus, during preparation for surgery, the patient's head, in addition to being swathed in sterile fabric except around the eye, will be raised above table 12 by interposing cushions or pads, sometimes called doughnuts, sufficient to raise the eye, hence, the surgical situs, to the plane A—A which includes support surfaces 14, 14 usefully employed by the surgeon as he operates on the eye. In other words, the surgical situs, i.e., the eye under consideration, and the laterally disposed support surfaces 14, 14 are coplanar.

The closed end 25 of block 10 is thin and functions as a hinge when it is being disposed about the patient's swathed, sanitized and otherwise prepared head. A nurse grasps the two ends of block 10 and flexes them to spread the front of opening 18 to wider separation. She then moves the block 10 into contact with the top of the patient's head and allows the lobes or shoulders 19, 19 to close together intimately with the sides of the neck and shoulders of the patient.

When preparation is complete, a sterile, surgical drape (indicated by dashed line 28 in FIG. 1) covers the patient's head and block 10 as shown. Drape 28 will have an opening (not shown) through which the surgeon has access to the eye. The drape 28 lies flat on surfaces 14, 14 of block 10 about the surgical situs.

During eye surgery surfaces 14, 14 function as nonrigid, slightly resilient hand and wrist rests for the surgeon, and provide closely and conveniently located platforms or depositories for surgical instruments and ocular appliances. The coplanar disposition of surfaces 14, 14 and the patient's eye 16 is of extreme importance in eye surgery, some of the most delicate known to surgeons. Care should be exercised in the choice of the resilient material from which block 10 is formed. It is desirable that it have a degree of resilience and softness comfortable to the surgeon and the patient, and at the same time, sufficient firmness to constitute a reliable support, as well as to secure the patient's head against involuntary or inadvertent, reflexive movement as when under local anesthesia. Experience has shown that a urethane foam weighing about 5 to 7 pounds, preferably about 6 pounds per cubic foot, is satisfactory. The choice of material from which block 10 is formed includes consideration of its ability to be sterilized. There are available polyether foam materials that are autoclavable. At present the preferred foam material averages 0.51 psi. and is rated as "compressive resistant" determined by measuring at 25% deformation according to ASTM Standard D2406 for such testing.

It will be noted that when a surgeon bears down on block 10 he only applies pressure through the block to the table since the head is independently supported. If the head were supported on the same resilient block as that supporting the surgeon's hands and wrists, pressure on the block could cause the patient's head to turn and roll, thus risking injury or harm to the eye. To avoid this is a distinct advantage. Another advantage arises from the very close disposition of surfaces 14 to the surgical situs. This supports the heel of the surgeons hand as well as his wrist, and permits him to limit movement to his dextrous fingers as he manipulates his instruments.

In compliance with the statute, the invention has been described in language more or less specific as to structural features. It is to be understood, however, that the invention is not limited to the specific features shown, since the means and construction herein disclosed comprises a preferred form of putting the invention into effect. The invention is, therefore, claimed in any of its forms or modifications within the legitimate and valid scope of the appended claims, appropriately interpreted in accordance with the doctrine of equivalents.

What is claimed is:

1. A head positioner and surgeon's arm rest for eye surgery and the like on a patient lying prone on a surgical table, comprising:
   a substantially right-rectangular block of resilient material to rest on the head end of said table;
   said block including a U-shaped patient's head-receiving, top-to-bottom open cavity, having an access passage open toward the foot of said table, the portions of said block forming the access passage converging to embrace the sides of the patient's neck above the shoulders;
   said cavity and access passage being shaped to receive and substantially embrace the sides of the patient's head; and
   said block being of a thickness to provide an upper horizontal support and work surface at each side of the patient's head substantially coplanar with the general plane of the surgical situs on the patient whose head is disposed in said cavity.

* * * * *